United States Patent [19]

Slusarchyk et al.

[11] 4,129,731

[45] Dec. 12, 1978

[54] PROCESS FOR CONVERTING 3-METHYLENE CEPHALOSPORINS TO 3-HETEROTHIOMETHYL CEPHALOSPORINS

[75] Inventors: William A. Slusarchyk, Belle Mead; Eric M. Gordon, West Trenton; William H. Koster, Pennington, all of N.J.

[73] Assignee: E. R. Squibb & Sons, Inc., Princeton, N.J.

[21] Appl. No.: 748,426

[22] Filed: Dec. 8, 1976

[51] Int. Cl.$^2$ .............................................. C07D 501/04
[52] U.S. Cl. ............................................ 544/21; 544/26; 544/27
[58] Field of Search .............. 260/243 C; 544/26, 27, 544/21

[56] References Cited

U.S. PATENT DOCUMENTS

| | | | |
|---|---|---|---|
| 3,275,626 | 9/1966 | Morin et al. | 260/243 C |
| 3,792,995 | 2/1974 | Ochiai et al. | 204/72 |
| 3,883,518 | 5/1975 | Ponticello et al. | 260/243 C |
| 3,925,372 | 12/1975 | Chauvette | 260/243 C |
| 3,929,775 | 12/1975 | Ochiai et al. | 260/243 C |
| 3,932,393 | 1/1976 | Chauvette | 260/243 C |
| 3,941,779 | 3/1976 | Slusarchyk et al. | 260/243 C |
| 3,962,227 | 6/1976 | Chauvette | 260/243 C |
| 3,968,109 | 6/1976 | Koster et al. | 260/243 C |
| 4,039,534 | 8/1977 | Slusarchyk et al. | 544/17 |
| 4,049,806 | 9/1977 | Beeby | 424/246 |

OTHER PUBLICATIONS

Wright et al, Chemical Abstracts, vol. 75, 76705c (1971).
Kaiser et al., J. Med. Chem., vol. 14, No. 5, pp. 426-429 (1971).
Ochiai et al., J. Chem Soc. Chem. Comm., 1972, pp. 800-801.
Ochiai et al., J. Chem Soc., Perkin I, 1974 pp. 258-262.
Ochiai et al., Tetrahedron Letters, No. 23, pp. 2345-2348, 1972.
Ochiai et al., Tetrahedron, vol. 31, pp. 115-122, 1975.
Chauvett et al, J. Org. Chem. vol. 38, pp. 2994-2999, 1973.

Primary Examiner—Paul M. Coughlan, Jr.
Assistant Examiner—Diana G. Rivers
Attorney, Agent, or Firm—Lawrence S. Levinson; Merle J. Smith; Stephen B. Davis

[57] ABSTRACT

This invention relates to the preparation of 3-heterothiomethyl cephalosporanic acid esters of the formula

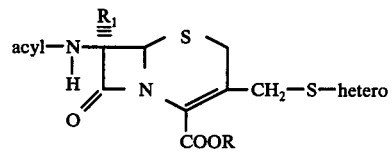

by treating a 3-methylene cephalosporin of the formula

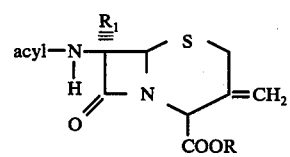

with a compound of the formula hetero-S-S-hetero or X-S-hetero in the presence of a base wherein R is a readily removable ester group, $R_1$ is in the α-configuration and is hydrogen or methoxy, and X is a leaving group. The resulting 3-heterothio cephalosporin esters are treated according to known methods to remove the ester protecting group and yield the corresponding free acids which have antibacterial activity.

10 Claims, No Drawings

PROCESS FOR CONVERTING 3-METHYLENE CEPHALOSPORINS TO 3-HETEROTHIOMETHYL CEPHALOSPORINS

BACKGROUND OF THE INVENTION

3-Methylene cephalosporanic acid esters are described as a by product in the conversion of penicillin sulfoxides to cephalosporins by Morin et al. in U.S. Pat. No. 3,275,626.

Additional methods for preparing acylated 3-methylene cephalosporin esters and their conversion to the corresponding 3-methyl compounds are disclosed by Chauvette in U.S. Pat. No. 3,932,393 and in J. Org. Chem., Vol. 38, p. 2994–2999. Chauvette in U.S. Pat. Nos. 3,925,372 and 3,962,227 describes converting the 3-methylene cephalosporins to the corresponding 3-hydroxy compound which can then be converted to a 3-halo cephalosporin.

Ponticello et al. in U.S. Pat. No. 3,883,518 describe the preparation of various acylated 3-methylene cephalosporins including those having a 7α-methoxy substituent. Ponticello et al. describe reacting the methylene compound with a source of halogen to yield an acylated 3-halo-3-halomethyl cephalosporin which is treated with base to yield the acylated 3-halomethyl compound.

Others methods of preparing acylated 3-methylene cephalosporins and their conversion to acylated 3-methyl cephalosporins are described by Ochiai et al. in U.S. Pat. Nos. 3,792,995 and 3,929,775 and in J.C.S. Chem. Comm., 1972, p. 800–801, Tetrahedron Letters, Vol. 23, p. 2341, J.C.S. Perkin I, 1974, p. 258–262, and Tetrahedron, Vol. 31, p. 115–122.

Various acylated 7α-methoxy and desmethoxy cephalosporins having a heterothiomethyl group in the 3-position are disclosed as possessing useful antibacterial activity as note U.S. Pat. Nos. 3,516,997, 3,641,021, 3,759,904, 3,821,207, 3,855,213, 3,867,380, 3,920,639, 3,978,051, 3,989,697, etc.

SUMMARY OF THE INVENTION

This invention relates to the preparation of 3-heterothiomethyl cephalosporanic acid esters of the formula

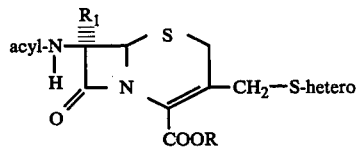
(I)

in a one step process by treating a 3-methylene compound of the formula

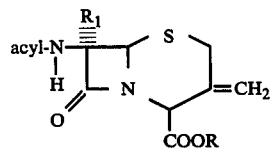
(II)

with a compound of the formula

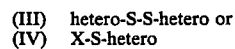

(III) hetero-S-S-hetero or
(IV) X-S-hetero in the presence of a base.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 4 carbon atoms. Examples of the type of groups contemplated are methyl, ethyl, n-propyl, isopropyl, t-butyl, etc. The lower alkoxy groups include such lower groups attached to an oxygen, e.g., methoxy, ethoxy, propoxy, etc.

R represents a readily removable ester group such as t-butyl, diphenylmethyl, trimethylsilyl, t-butyl dimethylsilyl, benzyl, p-methoxybenzyl, p-nitrobenzyl, or 2,2,2-trichloroethyl.

$R_1$ is in the α-configuration and is hydrogen or methoxy.

The term "hetero" represents the following groups

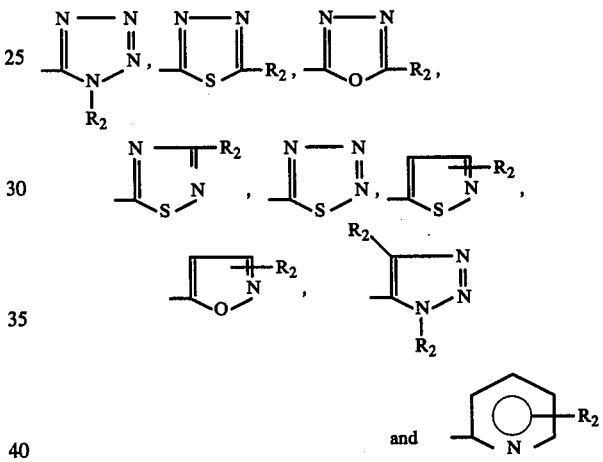

wherein $R_2$ is hydrogen or lower alkyl 1 to 4 carbons (preferably methyl or ethyl).

The term "acyl" represents those sidechains known in the cephalosporin art which can withstand the reaction with the compound of formula III or IV and which have been coupled with or are readily modified to provide sidechains that have been coupled with the cephalosporin nucleus to provide antibacterially active compounds, or which can be readily cleaved to yield the corresponding 7β-amino-7α-methoxy or desmethoxy-3-heterothiomethyl cephalosporanic acid ester. Exemplary acyl groups include lower

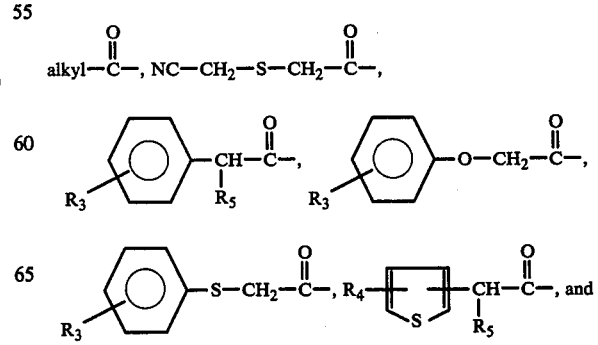

-continued

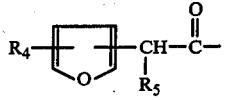

wherein $R_3$ is hydrogen, Cl, Br, lower alkyl (preferably methyl or ethyl), or lower alkoxy (preferably methoxy or ethoxy), $R_4$ is hydrogen, Cl, Br, or lower alkyl (preferably methyl or ethyl), and $R_5$ is hydrogen or protected amino of the formula

or protected hydroxy of the formula $-O-R_7$ wherein $R_6$ is t-butyl-oxycarbonyl, benzylcarbonyl, substituted benzyloxycarbonyl wherein the substituent is on the phenyl ring and is methyl, methoxy, nitro, Br or Cl, trichloroethyloxycarbonyl, adamantyloxycarbonyl, trifluoroacetyl, chloroacetyl, succinyl, phthaloyl, or formyl, preferably t-butyloxycarbonyl, substituted or unsubstituted benzyloxycarbonyl, and trichloroethyloxycarbonyl, and $R_7$ is trimethylsilyl or dichloroacetyl or other commonly employed protecting groups.

X represents halogen, i.e. Br, Cl, F, or I, preferably Br or Cl, lower alkoxycarbonylthio, preferably methoxycarbonylthio, phthalimido, succinimido, or a sulfonyl of the formula

wherein Z is lower alkyl, phenyl, or phenyl having a methyl, methoxy, nitro, Br, or Cl substituent.

The reaction between the 3-methylene compound of formula II and the thiolating compound of formula III or IV is performed in an inert organic solvent and in the presence of one or two equivalents of an alkali metal base or an organic base at a temperature of from about −80° C to about 20° C for from about 5 minutes to about 3 hours. Preferably the reaction is performed under an inert atmosphere such as nitrogen or argon.

Suitable inert organic solvents for this reaction include tetrahydrofuran, ethyl ether, dioxane, acetonitrile, dimethoxyethane, dimethylformamide, dimethylsulfoxide, and dimethylacetamide.

Suitable alkali metal bases include potassium t-butoxide, lithium diethylamide, lithium diisopropylamide, lithium N-cyclohexylisopropylamide, and lithium hexamethyldisilzane.

Suitable organic bases include 1,5-diazobicyclo-[5.4.0]undec-5-ene and 1,5-diazabicyclo[4.3.0]non-5-ene.

The 3-heterothiomethyl cephalosporanic acid ester of formula I prepared according to this invention can be treated in several ways to yield a valuable antibacterially active compound. When the acyl sidechain of the compound of formula I is the desired acyl sidechain of the antibacterially active compound, i.e. where acyl is phenylacetyl, (2-thienyl)acetyl, etc., then the only additional process involves removal of the carboxylic acid ester protecting group by acidic or basic hydrolysis as known in the art.

When the acyl sidechain of the compound of formula I contains a protected amino or protected hydroxy substituent then the additional process steps would involve removal of this protecting group as well as removal of the carboxylic acid ester protecting group according to methods known in the art as note, for example, U.S. Pat. Nos. 3,641,021, 3,796,801, 3,932,393, 3,855,213, etc. Also, the resulting α-amino compound can be reacted with an alkali metal cyanate or alkaline earth metal cyanate as taught in U.S. Pat. Nos. 3,978,051 and 3,989,697 to yield the corresponding α-ureido compound or reacted according to the procedure of U.S. Pat. No. 3,925,368 or 3,956,292 to yield various α-acylated ureido compounds.

In other instances, for example where acyl is lower

it is preferred to deacylate the compound of formula I according to known procedures to yield the corresponding 7β-amino-7α-methoxy or desmethoxy-3-heterothiomethyl cephalosporanic acid ester which can then be acylated to introduce a different 7β-position sidechain.

The following examples are illustrative of the invention. All temperatures are expressed in degrees centigrade.

EXAMPLE 1

3-[[(1-Methyl-1H-tetrazol-5-yl)thio]methyl]-8-oxo-7β-[(phenylacetyl)amino]-5-thia-1-azabicyclo[4.2.0]oct-2-ene-2-carboxylic acid 149 μl. (0.6 mmol.) of bis(trimethylsilyl)acetamide is added to a stirred solution of 166 mg. (0.5 mmol.) of 3-methylene-8-oxo-7β-[(phenylacetyl]amino]-5-thia-1-azabicyclo[4.2.0]oct-2-ene-2-carboxylic acid in 10 ml. of dry tetrahydrofuran at 0° under a nitrogen atmosphere. The mixture is stirred for 15 minutes at 0° and 230 mg. (1 mmol.) of (1-methyl-1H-tetrazol-5-yl)disulfide is added. The mixture is cooled to −70° C and 83 μl. (0.5 mmol.) of 1,5-diazobicyclo[5.4.0]undec-5-ene is added. The mixture is stirred at −70° for 1 hour and then allowed to warm to 0° over the course of 30 minutes. Ethyl acetate and water are added and the pH is adjusted to 7.5 by the addition of aqueous sodium bicarbonate. The aqueous layer is extracted twice more with ethyl acetate and then layered with fresh ethyl acetate. The pH is adjusted to 2.0 by the addition of 1N HCl and after repeated extractions with ethyl acetate, the combined acidic ethyl acetate extract is dried (Na$_2$SO$_4$) and evaporated to a residue of 277 mg. of crude 3-[[(1-methyl-1H-tetrazol-5-yl)thio]methyl]-8-oxo-7β-[(phenylacetyl]amino]-5-thia-1-azabicyclo [4.2.0]-oct-2-ene-2-carboxylic acid: PMR (DCCl$_3$-CD$_3$OD) δ 3.62 (2H,s, Ar-CH$_2$—), 3.70 (2H,sC-2), 3.97 (3H,s,N—CH$_3$), 4.37 (2H,s,C-3'), 5.03 (1H,d,J=5Hz,C-6), 5.73 (1H,d, J=5Hz,C-7), and 7.33 (5Hz,s,aromatics).

The residue is purified by chromatography on three 20 × 20 × cm. × 1 mm. silica gel plates in the system acetone-acetic acid (16:1). Elution of the band R$_f$ ∼ 0.6 with acetone-methanol (3:1) followed by removal of the solvent yields a residue. The residue is taken up in ethyl acetate-water, the pH is adjusted to 7.5 by the addition of aqueous sodium bicarbonate, and after extracting, the aqueous layer is covered with fresh ethyl acetate and the pH adjusted to 2 by the addition of 1N HCl. After repeated extraction with ethyl acetate, the combined acidic ethyl acetate extract is dried (Na₂SO₄) and evaporated to yield 88 mg. of 3-[[(1-methyl-1H-tetrazol-5-yl)thio]methyl]-8-oxo-7β-[(phenylacetyl]-amino]-5-thia-1-azabicyclo[4.2.0]oct-2-ene-2-carboxylic acid: PMR (DCCl₃) δ 3.65 (2H,s,Ar-CH₂—), 3.70 (2H,s,C-2), 3.83 (3H,s,N-CH₃), 4.32 (2H,broad, s,C-3'), 4.97 (1H,d,J=5Hz,C-6), 5.90 (1H,q,J=5Hz,J=8Hz,C-7), 6.97 (1H,s,

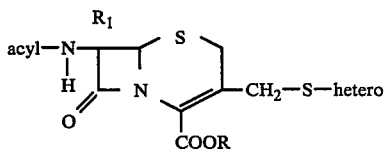

and 7.33 (15H,broad s, aromatics).

EXAMPLE 2

3-[[(1-Methyl-1H-tetrazol-5-yl)thio]methyl]-8-oxo-7β-[(phenylacetyl)amino]-5-thia-1-azabicyclo[4.2.0]oct-2-ene-2-carboxylic acid, diphenylmethyl ester A solution of 200 mg. (0.4 mmol.) of 3-methylene-8-oxo-7β-[(phenylacetyl]amino]-5-thia-1-azabicyclo[4.2.0]-oct-2-ene-2-carboxylic acid, diphenylmethyl ester in 1 ml. of tetrahydrofuran is added to a stirred solution of lithium N-cyclohexylisopropylamide (prepared from 0.36 ml. of 2.4 M n-butyl lithium in hexane and 0.147 ml. of N-cyclohexylisopropylamine in 4 ml. of tetrahydrofuran) at −70° under a nitroen atmosphere followed in 15 seconds by the addition of a solution of 184 mg. (0.8 mmol.) of (1-methyl-1H-tetrazol-5-yl)disulfide in 5 ml. of tetrahydrofuran. The mixture is stirred at −70° for 30 minutes and then poured into a pH 6.6 phosphate buffer and ethyl acetate. After repeated extraction with ethyl acetate, the combined ethyl acetate extract is washed successively with dilute HCl, water, and saturated NaCl solution. After drying (MgSO₄), the ethyl acetate extract is evaporated in vacuo to yield 278 mg. of crude product. This residue is purified by thin layer chromatography on silica gel in the system chloroform-ethyl acetate (3:1) to yield 39 mg. of 3-[[(1-methyl-1H-tetrazol-5-yl)thio]-methyl]-8-oxo-7β-[(phenylacetyl]amino]-5-thia-1-azabicyclo-[4.2.0]oct-2-ene-2-carboxylic acid, diphenylmethyl ester.

EXAMPLE 3

3-[[(1-Methyl-1H-tetrazol-5-yl)thio)methyl]-8-oxo-7β-[(phenylacetyl)amino]-5-thia-1-azabicyclo[4.2.0]oct-2-ene-2-carboxylic acid, diphenylmethyl ester 0.5 mmol. of 1,5-diazobicyclo[5.4.0]undec-5-ene is added to a stirred solution of 0.5 mmol. of 3-methylene-8-oxo-7β-[(phenylacetyl)amino]-5-thia-1-azabicyclo[4.2.0]-oct-2-ene-2-carboxylic acid, diphenylmethyl ester and 1 mmol. of (1-methyl-1H-tetrazol-5-yl)disulfide in 10 ml. of dry tetrahydrofuran at −75° under a nitrogen atmosphere. The mixture is stirred at −75° for 2 hours and then allowed to warm to 0°. Then 0.3 ml. of acetic acid is added followed by ethyl acetate and water. The pH is adjusted to 2 by the addition of 1N HCl and the ethyl acetate layer is washed with water and dilute sodium bicarbonate (pH ≃ 7). The ethyl acetate layer is dried (Na₂SO₄) and evaporated in vacuo to yield 265 mg. of crude product. This residue is purified by thin layer chromatography on silica gel in the system chloroform-ethyl acetate (3:1) to yield the purified 3-[[(1-methyl-1H-tetrazol-5-yl)thio]methyl]-8-oxo-7β-[(phenylacetyl)amino]-5-thia-1-azabicyclo[4.2.0]oct-2-ene-2-carboxylic acid, diphenylmethyl ester.

EXAMPLE 4

3-[[(1-Methyl-1H-tetrazol-5-yl)thio]methyl]-8-oxo-7β-[(phenylacetyl)amino]-5-thia-1-azabicyclo[4.2.0]oct-2-ene-2-carboxylic acid, diphenylmethyl ester A solution of 3 mmol. of 3-methylene-8-oxo-7β-[(phenylacetyl)amino]-5-thia-1-azabicyclo[4.2.0]oct-2-ene-2-carboxylic acid, diphenylmethyl ester in 15 ml. of tetrahydrofuran is added to a stirred solution of 6 mmol. of lithium N-cyclohexylisopropylamide in 30 ml. of tetrahydrofuran at −70° under a nitrogen atmosphere followed in 15 seconds by the addition of 6 mmol. of (1-methyl-1H-tetrazol-5-yl)thiotosylate in 15 ml. of tetrahydrofuran. The mixture is stirred at −70° for 30 minutes and then poured into a pH 6.6 phosphate buffer and ethyl acetate. After repeated extraction with ethyl acetate, the combined ethyl acetate extract is washed successively with dilute HCl, water, and saturated NaCl solution. After drying (MgSO₄), the ethyl acetate extract is evaporated in vacuo to yield 342 mg. of crude product. This residue is purified by thin layer chromatography on silica gel in the system chloroform-ethyl acetate (3:1) to yield the purified 3-[[(1-methyl-1H-tetrazol-5-yl)thio]methyl]-8-oxo-7β-[(phenylacetyl)amino]-5-thia-1-azabicyclo [4.2.0]-oct-2-ene-2-carboxylic acid, diphenylmethyl ester.

EXAMPLES 5–36

Following the procedures of examples 1 to 4 but employing the 3-methylene cephalosporin ester shown in Col. I and either the disulfide shown in Col. II or the compound shown in Col. III, one obtains the 3-heterothio cephalosporin ester shown in Col. IV.

| | Col. I | | | Col. II |
|---|---|---|---|---|
| | acyl-NH-[β-lactam-cephem with =CH₂]-COOR with R₁ | | | hetero-S—S-hetero |
| | Col. III | | | Col. IV |
| | X—S-hetero | | | acyl-NH-[cephem]-CH₂-S-hetero, COOR with R₁ |

| Ex. | acyl | $R_1$ | R | X | hetero |
|---|---|---|---|---|---|
| 5 | thiophen-2-yl-CH₂-C(O)- | —H | —t-C₄H₉ | Cl | 5-methyl-1,3,4-thiadiazol-2-yl |
| 6 | thiophen-3-yl-CH₂-C(O)- | —H | —CH₂-C₆H₅ | Br | 5-ethyl-1,3,4-thiadiazol-2-yl |
| 7 | (4-Cl-thiophen-2-yl)-CH₂-C(O)- | —H | —CH₂-C₆H₄-OCH₃ | CH₃-S(O)₂- | 1-methyl-1H-tetrazol-5-yl |
| 8 | (furan-2-yl)-CH₂-C(O)- | —OCH₃ | —CH₂-C₆H₄-NO₂ | C₆H₅-S(O)₂- | 5-methyl-1,3,4-oxadiazol-2-yl |
| 9 | (5-methyl-furan-3-yl)-CH₂-C(O)- | —H | —CH₂CCl₃ | H₃C-C₆H₄-S(O)₂- | 3-methylisothiazol-5-yl |
| 10 | (4-CH₃O-C₆H₄)-CH₂-C(O)- | —H | —CH(C₆H₅)₂ | O₂N-C₆H₄-S(O)₂- | 4-methylisoxazol-5-yl |
| 11 | (4-Cl-C₆H₄)-CH₂-C(O)- | —OCH₃ | —CH₂-C₆H₄-NO₂ | CH₃-O-C(O)-S- | 4-methyl-1,3-thiazol-2-yl |
| 12 | (4-CH₃-C₆H₄)-CH₂-C(O)- | —H | —Si(CH₃)₃ | Cl | 1,3,4-thiadiazol-2-yl |
| 13 | (3-C₂H₅O-C₆H₄)-CH₂-C(O)- | —H | —CH(C₆H₅)₂ | Br | 1H-1,2,3-triazol-4-yl |
| 14 | C₆H₅-S-CH₂-C(O)- | —H | —CH(C₆H₅)₂ | CH₃-S(O)₂- | 4-methyl-1H-1,2,3-triazol-5-yl |
| 15 | C₆H₅-O-CH₂-C(O)- | —H | —CH₂-C₆H₄-OCH₃ | Cl-C₆H₄-S(O)₂- | 1-methyl-1H-1,2,3-triazol-5-yl |

-continued

| | Col. I<br>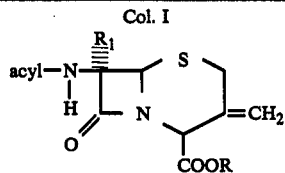 | | | Col. II<br>hetero-S—S-hetero | |
|---|---|---|---|---|---|
| | Col. III<br>X—S-hetero | | | Col. IV<br>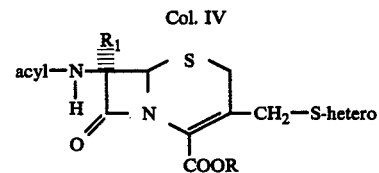 | |
| Ex. | acyl | $R_1$ | R | X | hetero |
| 16 | NC—CH$_2$—S—CH$_2$—C(=O)— | —H | —CH(—C$_6$H$_5$)$_2$ | Cl | 5-methyl-1-methyl-tetrazolyl |
| 17 | NC—CH$_2$—S—CH$_2$—C(=O)— | —OCH$_3$ | —CH(—C$_6$H$_5$)$_2$ | Cl | 5-methyl-1-methyl-tetrazolyl |
| 18 | C$_2$H$_5$—C(=O)— | —H | —CH(—C$_6$H$_5$)$_2$ | phthalimido (N-methyl) | 4-methyl-1-methyl-triazolyl |
| 19 | C$_3$H$_7$—C(=O)— | —H | —CH$_2$—C$_6$H$_4$—NO$_2$ | N-methyl-glutarimido | pyridyl |
| 20 | 2-thienyl-CH(NH-C(=O)-O-C(CH$_3$)$_3$)-C(=O)— | —OCH$_3$ | —CH(—C$_6$H$_5$)$_2$ | Cl | 5-methyl-1-methyl-tetrazolyl |
| 21 | 3-thienyl-CH(NH-C(=O)-O-CH$_2$-C$_6$H$_5$)-C(=O)— | —OCH$_3$ | —Si(CH$_3$)$_2$—C(CH$_3$)$_3$ | Br | 2-methyl-1,3,4-thiadiazolyl |
| 22 | 5-methyl-2-furyl-CH(NH-C(=O)-O-CH$_2$-C$_6$H$_4$-OCH$_3$)-C(=O)— | —H | —Si(CH$_3$)$_3$ | CH$_3$—O—C(=O)—S— | 5-methyl-1,3,4-oxadiazolyl |

-continued

| | Col. I | | | Col. II |
|---|---|---|---|---|
| | acyl-NH-[β-lactam with R₁, S, =CH₂, COOR] | | | hetero-S—S-hetero |
| | Col. III | | | Col. IV |
| | X—S-hetero | | | acyl-NH-[cephem with R₁, CH₂-S-hetero, COOR] |

| Ex. | acyl | R₁ | R | X | hetero |
|---|---|---|---|---|---|
| 23 | furan-2-yl-CH(NH-C(=O)-O-CH₂CCl₃)-C(=O)- | —OCH₃ | —CH(C₆H₅)₂ | CH₃—S(=O)₂— | triazole-NH |
| 24 | furan-3-yl-CH(NH-C(=O)-O-C(CH₃)₃)-C(=O)- | —H | —CH₂-C₆H₄-OCH₃ | Cl | 3-methylpyridine |
| 25 | 5-chlorofuran-2-yl-CH(NH-C(=O)-O-CH₂CCl₃)-C(=O)- | —OCH₃ | —CH₂-C₆H₄-NO₂ | Br | 4-methylisothiazole |
| 26 | C₆H₅-CH(NH-C(=O)-O-CH₂-C₆H₅)-C(=O)- | —H | —CH₂CCl₃ | H₃C-C₆H₄-S(=O)₂— | 1-methyltetrazole |
| 27 | H₃C-C₆H₄-CH(NH-C(=O)-O-CH₂-C₆H₄-OCH₃)-C(=O)- | —OCH₃ | —CH(C₆H₅)₂ | CH₃—S(=O)₂— | 1-methyltetrazole |
| 28 | H₃CO-C₆H₄-CH(NH-C(=O)-O-C(CH₃)₃)-C(=O)- | —OCH₃ | —Si(CH₃)₃ | Cl | 1-methyltetrazole |

-continued

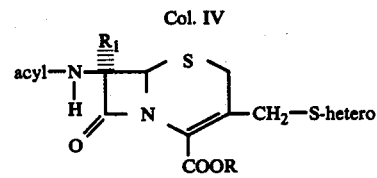

| Ex. | acyl | $R_1$ | R | X | hetero |
|---|---|---|---|---|---|
| 29 | 3-Cl-C₆H₄-CH(NHCOOC(CH₃)₃)-CO- | $-OCH_3$ | $-CH(C_6H_5)_2$ | Br | 1-methyl-tetrazol-5-yl |
| 30 | 4-CH₃-C₆H₄-CH(NHCOOC(CH₃)₃)-CO- | $-H$ | $-CH(C_6H_5)_2$ | $H_3C-C_6H_4-SO_2-$ | 1-methyl-triazol-5-yl |
| 31 | 4-Br-C₆H₄-CH(NHCOOCH₂C₆H₅)-CO- | $-OCH_3$ | $-CH(C_6H_5)_2$ | $H_3C-O-CO-S-$ | 1-methyl-tetrazol-5-yl |
| 32 | C₆H₅-CH(NHCOOCH₂C₆H₅)-CO- | $-OCH_3$ | $-CH(C_6H_5)_2$ | Cl | 1-methyl-tetrazol-5-yl |
| 33 | C₆H₅-CH(OSi(CH₃)₃)-CO- | $-H$ | $-Si(CH_3)_3$ | $CH_3-SO_2-$ | 1-methyl-tetrazol-5-yl |
| 34 | C₆H₅-CH(OSi(CH₃)₃)-CO- | $-OCH_3$ | $-CH(C_6H_5)_2$ | Cl | 2-methyl-1,3,4-thiadiazol-5-yl |
| 35 | 4-Cl-C₆H₄-CH(OCOCHCl₂)-CO- | $-H$ | $-CH_2-C_6H_4-OCH_3$ | Br | 1-methyl-tetrazol-5-yl |

-continued

| Col. I | Col. II |
|---|---|
| 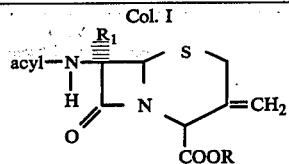 | hetero-S—S-hetero |
| Col. III | Col. IV |
| X—S-hetero | 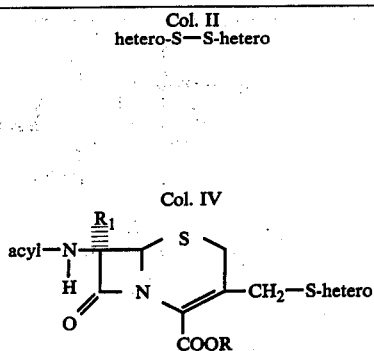 |

| Ex. | acyl | R₁ | R | X | hetero |
|---|---|---|---|---|---|
| 36 | 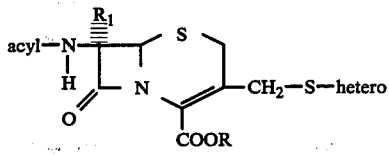 | —H | 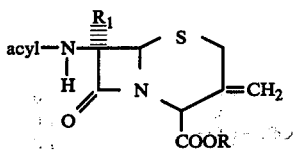 | 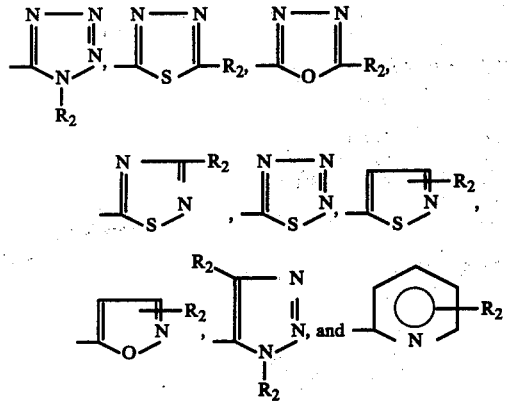 | |

In examples 12, 21, 22, 28 and 33 involving a silyl ester, the isolated product of Col. IV will be in the form of the free acid (i.e. R is hydrogen) as in example 1 since the silyl ester is hydrolyzed off during the extraction steps.

What is claimed is:

1. A process for the preparation of a compound of the formula acyl—NH—[...]—CH₂—S—hetero
COOR which comprises reacting a 3-methylene compound of the formula acyl—NH—[...]=CH₂
COOR in an inert organic solvent with either a disulfide of the formula hetero-S-S-hetero or a compound of the formula X-S-hetero in the presence of an alkali metal base or an organic base at a temperature of from about −80° C to about 20° C for from about 5 minutes to about 3 hours; wherein R is a readily removable ester group; R₁ is in the α-configuration and is hydrogen or methoxy; hetero is selected from the group consisting of

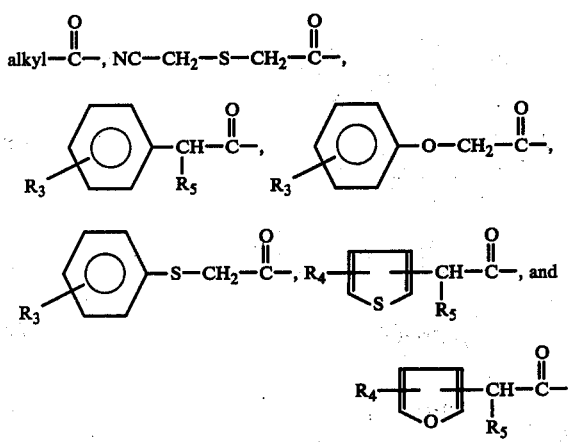

wherein $R_2$ is hydrogen or lower alkyl 1 to 4 carbons; acyl is selected from the group consisting of lower alkyl—C(O)—, NC—CH₂—S—CH₂—C(O)—,

[phenyl]—CH(R₅)—C(O)—, [phenyl]—O—CH₂—C(O)—,
R₃                    R₃

[phenyl]—S—CH₂—C(O)—, R₄—[thienyl]—CH(R₅)—C(O)—, and
R₃

R₄—[furyl]—CH(R₅)—C(O)— wherein $R_3$ is hydrogen, Cl, Br, lower alkyl, or lower alkoxy, $R_4$ is hydrogen, Cl, Br, or lower alkyl, and $R_5$ is hydrogen, protected amino, or protected hydroxy; and X is halogen, lower alkoxycarbonylthio, phthalimido, succinimido, or

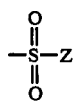

wherein Z is lower alkyl, phenyl, or phenyl having a methyl, methoxy, nitro, Br, or Cl substituent.

2. The process of claim 1 wherein R is selected from the group consisting of t-butyl, benzyl, p-nitro-benzyl, p-methoxybenzyl, diphenylmethyl, trimethylsilyl, t-butyl dimethylsilyl and 2,2,2-trichloroethyl; $R_2$ is hydrogen, methyl, or ethyl; $R_3$ is hydrogen, Cl, Br, methyl, ethyl, methoxy, or ethoxy; $R_4$ is hydrogen, Cl, Br, methyl or ethyl; $R_5$ is hydrogen, protected amino of the formula

or protected hydroxy of the formula —O-$R_7$ wherein $R_6$ is t-butyloxycarbonyl, benzyloxycarbonyl wherein the phenyl ring has a hydrogen, methyl, methoxy, nitro, Br or Cl substituent, or trichloroethyloxycarbonyl and $R_7$ is trimethylsilyl or dichloroacetyl.

3. The process of claim 2 wherein the inert organic solvent is selected from the group consisting of tetrahydrofuran, ethyl ester, dioxane, acetonitrile, dimethoxyethane, dimethylformamide, dimethylsulfoxide, and dimethylacetamide; the alkali metal base is selected from the group consisting of potassium t-butoxide, lithium diethylamide, lithium diisopropylamide, lithium N-cyclohexylisopropylamide, and lithium hexamethyldisilzane; and the organic base is selected from the group consisting of 1,5-diazobicyclo[5.4.0]undec-5-ene and 1,5-diazobicyclo[4.3.0]non-5-ene.

4. The process of claim 3 wherein acyl is selected from the group consisting of

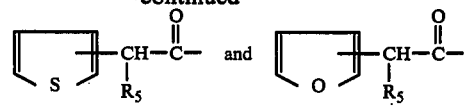

and $R_5$ is hydrogen

or -O-$R_7$ wherein $R_6$ is t-butyloxycarbonyl, benzyloxycarbonyl, p-methoxybenzyloxycarbonyl, or trichloroethyloxycarbonyl and $R_7$ is trimethylsilyl or dichloroacetyl.

5. The process of claim 4 wherein the base is 1,5-diazobicyclo[5.4.0]undec-5-ene or lithium N-cyclohexylisopropylamide.

6. The process of claim 5 wherein hereto is

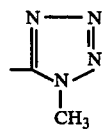

7. The process of claim 6 wherein $R_1$ is hydrogen.

8. The process of claim 7 wherein acyl is

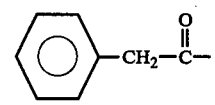

and R is diphenylmethyl.

9. The process of claim 7 wherein acyl is

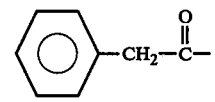

and R is trimethylsilyl.

10. The process of claim 5 wherein $R_1$ is methoxy.

* * * * *

UNITED STATES PATENT AND TRADEMARK OFFICE
CERTIFICATE OF CORRECTION

PATENT NO. : 4,129,731
DATED : December 12, 1978
INVENTOR(S) : William A. Slusarchyk et al.

It is certified that error appears in the above-identified patent and that said Letters Patent are hereby corrected as shown below:

Col. 5, the structure at line 11 should read:

Col. 6, line 51, -- in vacuo -- should be italicized.

Signed and Sealed this

Twenty-seventh Day of March 1979

[SEAL]

Attest:

RUTH C. MASON
Attesting Officer

DONALD W. BANNER
Commissioner of Patents and Trademarks